US009510804B2

(12) United States Patent
Lee et al.

(10) Patent No.: US 9,510,804 B2
(45) Date of Patent: Dec. 6, 2016

(54) REGION SETTING FOR INTIMA MEDIA THICKNESS MEASUREMENT IN AN ULTRASOUND SYSTEM

(75) Inventors: Jin Yong Lee, Seoul (KR); Jae Yoon Shim, Seoul (KR)

(73) Assignee: SAMSUNG MEDISON CO., LTD., Hongcheon-Gun, Gangwon-Do (KR)

( * ) Notice: Subject to any disclaimer, the term of this patent is extended or adjusted under 35 U.S.C. 154(b) by 1080 days.

(21) Appl. No.: 12/617,166

(22) Filed: Nov. 12, 2009

(65) Prior Publication Data

US 2010/0125202 A1  May 20, 2010

(30) Foreign Application Priority Data

Nov. 19, 2008 (KR) .......................... 10-2008-0115332

(51) Int. Cl.
*A61B 8/14* (2006.01)
*A61B 8/08* (2006.01)
(Continued)

(52) U.S. Cl.
CPC ......... *A61B 8/0858* (2013.01); *A61B 5/02007* (2013.01); *G06T 7/0012* (2013.01);
(Continued)

(58) Field of Classification Search
CPC ..................... A61B 5/02–5/02007; G06T 7/60
(Continued)

(56) References Cited

U.S. PATENT DOCUMENTS 5,469,850 A    11/1995  Iizuka
6,835,177 B2 * 12/2004  Fritz et al. .................... 600/443
(Continued)

FOREIGN PATENT DOCUMENTS

EP    0958784 A1    11/1999
EP    1728471 A1    12/2006
(Continued)

OTHER PUBLICATIONS

Inger Wendelhag,et al. "A new automated computerized analyzing system simplifies readings and reduces the variability in ultrasound measurement of intima-media thickness," Stroke, vol. 28, No. 11, Nov. 1997, pp. 2195-2200.
(Continued)

*Primary Examiner* — Serkan Akar
(74) *Attorney, Agent, or Firm* — McDermott Will & Emery LLP

(57) ABSTRACT

The present invention relates to an ultrasound system and a method of setting an intima-media thickness (IMT) measuring region. The ultrasound system comprises an ultrasound diagnosis unit configured to transmit ultrasound signals to a target object, receive ultrasound echo signals reflected from the target object and form an ultrasound image including a plurality of pixels based on the ultrasound echo signals, each pixel having an intensity of gray level. The ultrasound system further comprises a processor configured to compute intensities of the pixels at each row in the ultrasound image to form a first graph, compute first moving averages of the intensities for first subsets of rows in the ultrasound image by dividing the intensities by a thickness of a blood vessel to form a second graph, compute second moving averages of the intensities for second subsets of rows in the ultrasound image by dividing the intensities by a thickness of a vascular wall to form a third graph, and set an intima-media thickness (IMT) measuring region by using inflection points from the second and third graphs.

15 Claims, 5 Drawing Sheets

(51) Int. Cl.
    *A61B 5/02*      (2006.01)
    *G06T 7/00*      (2006.01)
    *G06T 7/60*      (2006.01)

(52) U.S. Cl.
    CPC .... *G06T 7/602* (2013.01); *G06T 2207/10132* (2013.01); *G06T 2207/30101* (2013.01)

(58) Field of Classification Search
    USPC ........ 382/100, 128, 131; 600/407, 427, 437, 600/441, 443, 449, 454, 458
    See application file for complete search history.

(56) References Cited

U.S. PATENT DOCUMENTS

| | | | |
|---|---|---|---|
| 7,727,153 B2 * | 6/2010 | Fritz et al. | 600/449 |
| 7,831,081 B2 * | 11/2010 | Li | 382/131 |
| 7,927,278 B2 * | 4/2011 | Selzer et al. | 600/443 |
| 7,955,265 B2 * | 6/2011 | Burla et al. | 600/458 |
| 8,047,989 B2 * | 11/2011 | Oshiki et al. | 600/437 |
| 8,103,066 B2 * | 1/2012 | Kim et al. | 382/128 |
| 2003/0199762 A1 * | 10/2003 | Fritz et al. | 600/437 |
| 2003/0229284 A1 * | 12/2003 | Stein | 600/454 |
| 2005/0096528 A1 * | 5/2005 | Fritz et al. | 600/407 |
| 2007/0038084 A1 * | 2/2007 | Burla et al. | 600/437 |
| 2007/0110291 A1 * | 5/2007 | Ahn et al. | 382/128 |
| 2007/0149877 A1 * | 6/2007 | Oshiki et al. | 600/427 |
| 2008/0044054 A1 * | 2/2008 | Kim et al. | 382/100 |
| 2008/0051658 A1 * | 2/2008 | Demi et al. | 600/441 |
| 2008/0097209 A1 * | 4/2008 | Lee et al. | 600/443 |
| 2008/0171939 A1 | 7/2008 | Ishihara | |
| 2008/0196506 A1 | 8/2008 | Satoh et al. | |

FOREIGN PATENT DOCUMENTS

| | | |
|---|---|---|
| JP | 11-318896 A | 11/1999 |
| JP | 2003-305039 A | 10/2003 |
| JP | 2008-0168016 A | 7/2008 |
| JP | 2008-194365 A | 8/2008 |

OTHER PUBLICATIONS

Korean Notice of Allowance, issued in Korean Patent Application No. 10-2008-0115332, dated May 8, 2012.

Japanese Notice of Allowance with English translation issued in Japanese Application No. 2009-260314 issued Nov. 19, 2013.

* cited by examiner

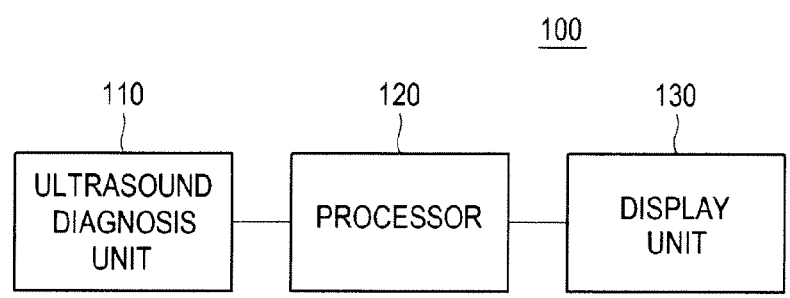
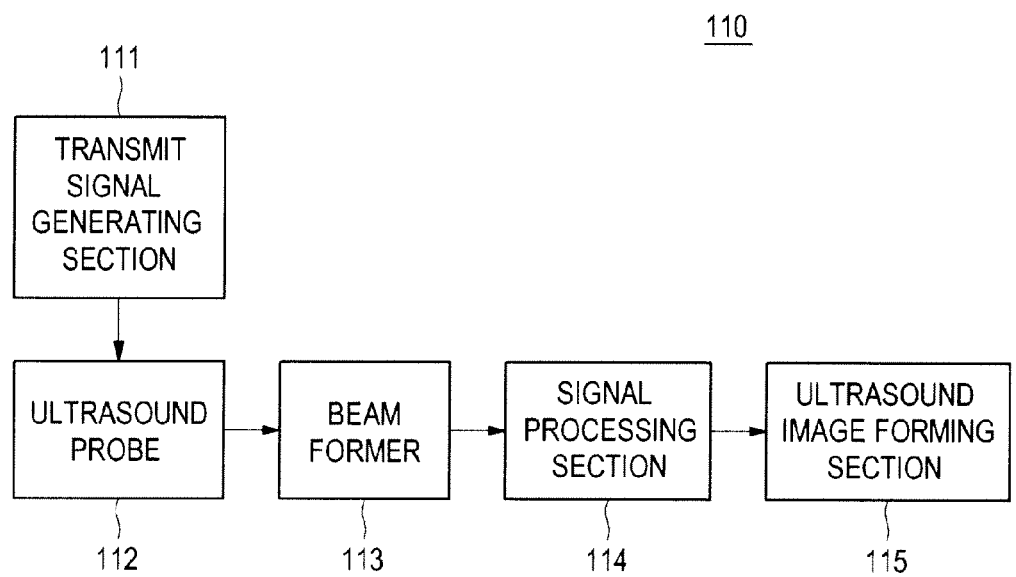

| $h_{11}$ | $h_{12}$ | $h_{13}$ | ... | $h_{1(n-1)}$ | $h_{1n}$ |
|---|---|---|---|---|---|
| $h_{21}$ | $h_{22}$ | $h_{23}$ | ... | $h_{2(n-1)}$ | $h_{2n}$ |
| $h_{31}$ | $h_{32}$ | $h_{33}$ | ... | $h_{3(n-1)}$ | $h_{3n}$ |
| $h_{41}$ | $h_{42}$ | $h_{43}$ | ... | $h_{4(n-1)}$ | $h_{4n}$ |
| ⋮ | ⋮ | ⋮ | ... | ⋮ | ⋮ |
| $h_{(m-1)1}$ | $h_{(m-1)2}$ | $h_{(m-1)3}$ | ... | ... | $h_{(m-1)(n-1)}$ |
| $h_{m1}$ | $h_{m2}$ | $h_{m3}$ | ... | $h_{m(n-1)}$ | $h_{mn}$ |

REGION SETTING FOR INTIMA MEDIA THICKNESS MEASUREMENT IN AN ULTRASOUND SYSTEM

The present application claims priority from Korean Patent Application No. 10-2008-0115332 filed on Nov. 19, 2008, the entire subject matter of which is incorporated herein by reference.

BACKGROUND OF THE INVENTION

1. Technical Field

The present invention generally relates to ultrasound systems, and more particularly to an ultrasound system for setting an intima-media thickness (IMT) measuring region.

2. Background Art

The ultrasound system has become an important and popular diagnostic tool due to its non-invasive and non-destructive nature. Modern high-performance ultrasound imaging diagnostic systems and techniques are commonly used to produce two or three-dimensional images of internal features of patients.

The carotid is one of the arteries in a human body, which connects the main artery of the heart with the cerebral artery to supply blood to the brain. Two carotids exist at left and right sides of the neck. About 80% of the blood which is supplied to the brain may pass through the carotid. The carotid has been frequently examined using an ultrasound system to accurately evaluate carotid stenosis and arteriosclerosis. Intima-media thickness (IMT) has been used as an index to indicate the degrees of carotid arteriosclerosis. The IMT represents a thickness between lining membrane and media of the carotid.

Generally, the IMT is repeatedly measured for a small region. However, this requires significant time and effort. Thus, various IMT measurement applications for automatically measuring the IMT have been developed to achieve easy and fast measurement. However, the user is required to directly set a measuring region, which makes it highly difficult to accurately measure the IMT.

BRIEF DESCRIPTION OF THE DRAWINGS

FIG. 1 is a block diagram showing an illustrative embodiment of an ultrasound system.

FIG. 2 is a block diagram showing an ultrasound diagnosis unit.

DETAILED DESCRIPTION OF THE INVENTION

Figures 3, 4:
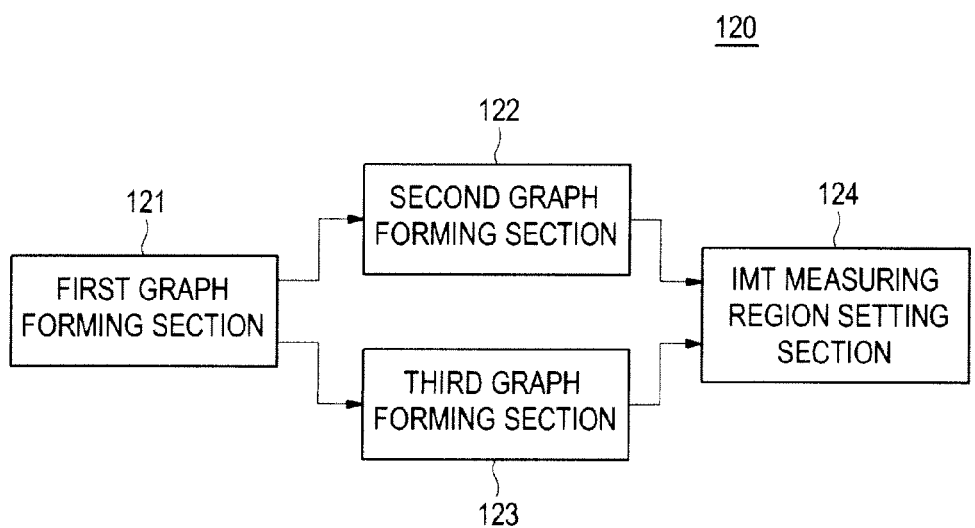
FIG. 3 is a schematic diagram showing an ultrasound image including a plurality of pixels.
FIG. 4 is a block diagram showing a processor.

FIG. 1 is a block diagram showing an illustrative embodiment of an ultrasound system. The ultrasound system 100 may include an ultrasound diagnosis unit 110, a processor 120 and a display unit 130.

The ultrasound diagnosis unit 110 may be configured to transmit ultrasound signals to a target object and receive ultrasound echo signals reflected from the target object. The ultrasound diagnosis unit 110 may be further configured to form ultrasound images of the target object based on the received ultrasound echo signals.

FIG. 2 is a block diagram showing the ultrasound diagnosis unit 110. The ultrasound diagnosis unit 110 may include a transmit (Tx) signal generating section 111, an ultrasound probe 112 including a plurality of transducer elements (not shown), a beam former 113, a signal processing section 114 and an ultrasound image forming section 115.

The Tx signal generating section 111 may generate Tx signals according to an image mode set in the ultrasound system 100. The image mode may include a brightness (B) mode, a Doppler (D) mode, a color flow mode, etc. In one embodiment, the B mode is set in the ultrasound system 100 to obtain a B mode image.

The ultrasound probe 112 may generate ultrasound signals, which may travel into the target object, in response to the Tx signals received from the Tx signal generating section 111. The ultrasound probe 112 may further receive ultrasound echo signals reflected from the target object and convert them into electrical receive signals. In such a case, the electrical receive signals may be analog signals. The electrical receive signals may correspond to a plurality of ultrasound image frames, which are obtained by repeatedly performing the transmission and reception of the ultrasound signals. The ultrasound probe 112 may be one of a three-dimensional probe, a two-dimensional probe, a one-dimensional probe and the like.

The beam former 113 may convert the electrical receive signals outputted from the ultrasound probe 112 into digital signals. The beam former 113 may further apply delays to the digital signals in consideration of distances between the transducer elements and focal points to thereby output receive-focused beams.

The signal processing section 114 may form a plurality of ultrasound data corresponding to the ultrasound image frames by using the receive-focused beams. The plurality of ultrasound data may be radio frequency (RF) data or IQ data.

The ultrasound image forming section 115 may form an ultrasound image of the target object based on the plurality of ultrasound data. Referring to FIG. 3, the ultrasound image may be formed with a plurality of pixels, each having an intensity of a gray level denoted by $h_{11}$-$h_{mn}$.

The processor 120, which is shown in FIG. 1, may analyze the ultrasound image to set an intima-media thickness (IMT) measuring region on the ultrasound image. The analysis of the ultrasound image for setting the IMT measuring region will be described in detail with reference to FIG. 4.

FIG. 4 is a schematic diagram showing the configuration of the processor 120. In one embodiment, the processor 120 may include a first graph forming section 121, a second graph forming section 122, a third graph forming section 123 and an IMT measuring region setting section 124.

In one embodiment, the first graph forming section 121 may compute average intensities of the pixels at each row in the ultrasound image to thereby form a first graph. The average intensities $f_k$ may be computed by using the following equation (1).

$$f_k = \frac{h_{k1} + h_{k2} + \ldots + h_{(k-1)(n-1)} + h_{kn}}{n} \quad (1)$$

wherein "k" indicates a row of pixels in the ultrasound image, wherein "k" ranges from 1 to m, and wherein "n" indicates a number of pixels in the same row.

In another embodiment, the first graph forming section 121 may compute sum intensities of the pixels at each row and form the first graph of the sum intensities with respect to the row of pixels in the ultrasound image.

Figure 5:
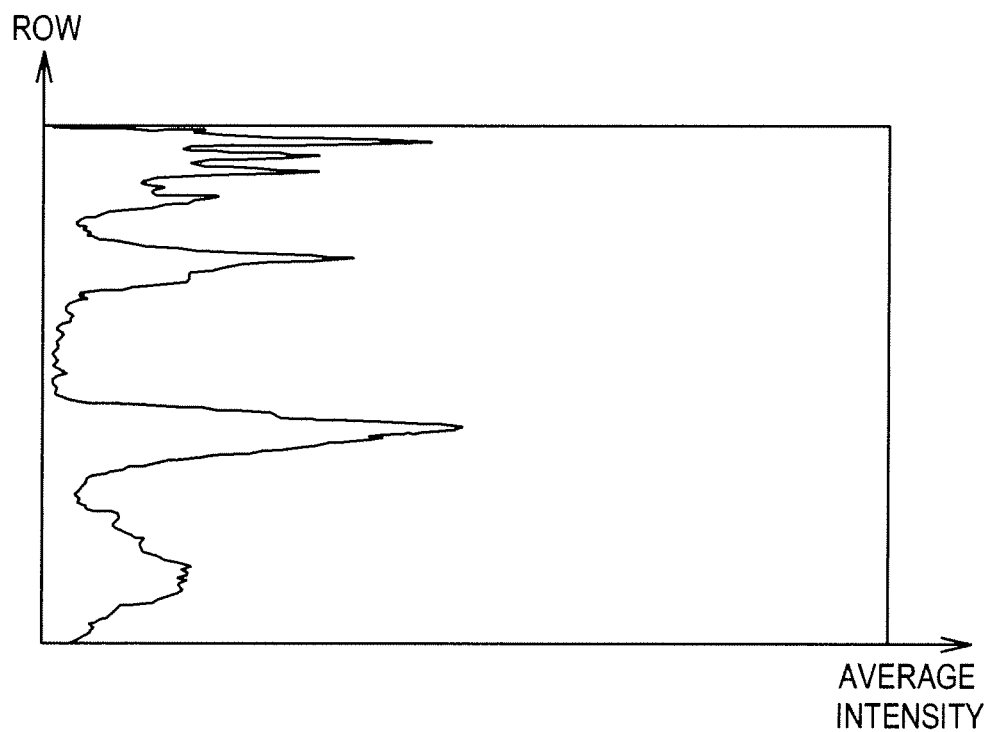
FIG. 5 is a schematic diagram showing a first graph.

As shown in FIG. 5, the first graph forming section 121 may form the first graph of the average intensities with respect to the row of pixels in the ultrasound image.

Figure 6:
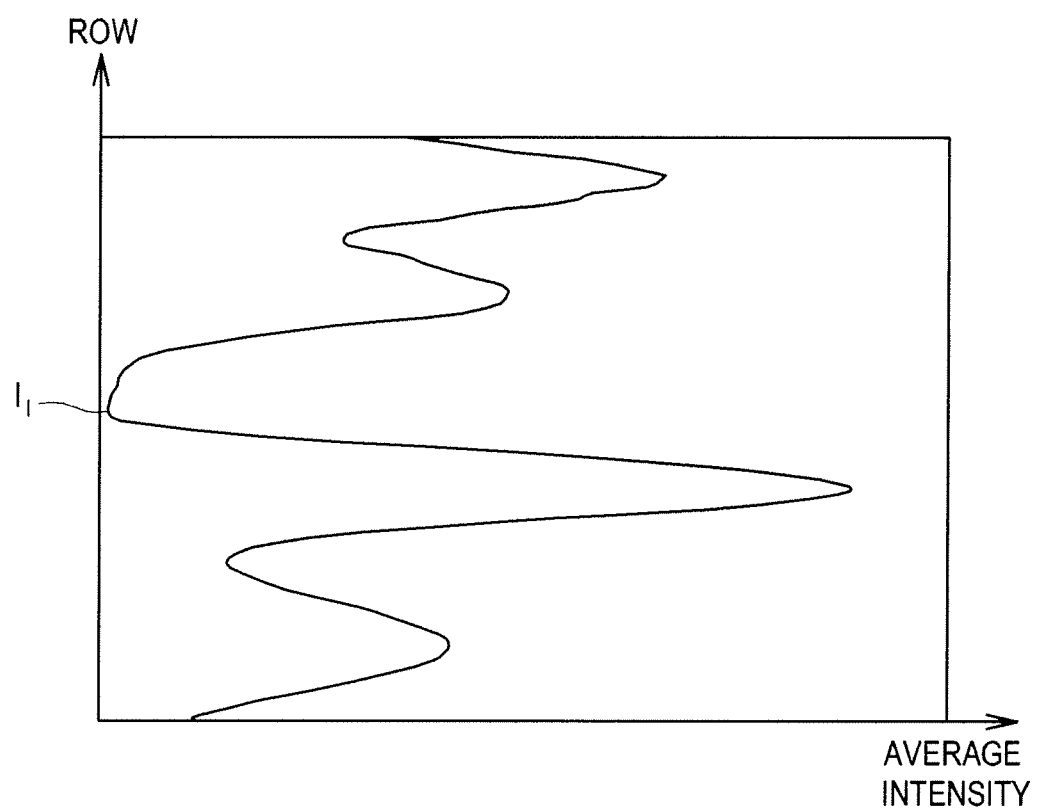
FIG. 6 is a schematic diagram showing a second graph and an inflection point.

The second graph forming section 122, which is shown in FIG. 4, may compute first moving averages of the average intensities for first subsets of the rows by dividing the intensities by a thickness of a blood vessel. As shown in FIG. 6, the second graph forming section 122 may form a second graph of the first moving averages with respect to the row of pixels in the ultrasound image. The blood vessel may be a carotid, although it is certainly not limited thereto. The first moving averages $MA_{11}$-$MA_{1m}$, may be computed by using the following equation (2).

$$MA_{11} = \frac{f_1 + f_2 + \ldots + f_{i-1} + f_i}{i} \quad (2)$$

$$MA_{12} = \frac{f_2 + f_3 + \ldots + f_i + f_{i+1}}{i}$$

$$\vdots$$

$$MA_{1m} = \frac{f_{m-i+1} + f_{m-i+2} + \ldots + f_{m-1} + f_m}{i}$$

wherein "i" indicates the number of pixels included within the thickness of blood vessel and "m" indicates the number of first moving averages. Generally, the thickness of the blood vessel may range from 2 to 5 mm. For example, assuming that the thickness of the carotid is about 3 mm and the height of the pixel is 0.5 mm, "i" becomes 6.

FIG. 6 shows the second graph of the first moving averages with respect to the rows of pixels in the ultrasound image. Referring back to FIG. 4, the IMT measuring region setting section 124 may detect a plurality of inflection points at which an inclination of curvatures on the second graph changes and selects the inflection point ("$I_1$" in FIG. 6) having a smallest moving average on the second graph.

Figure 7:
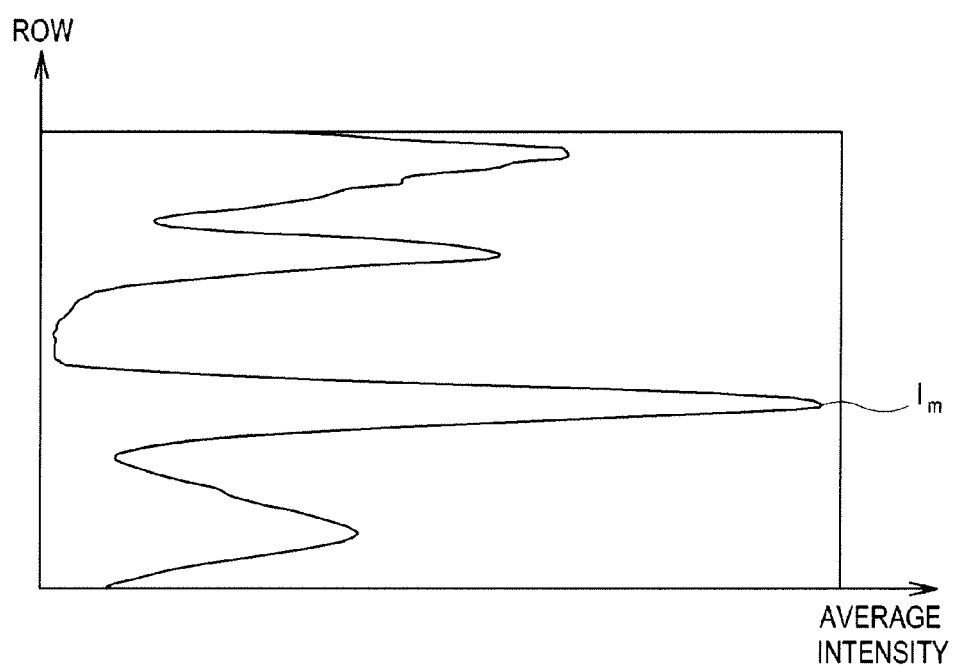
FIG. 7 is a schematic diagram showing a third graph and an inflection point.

The third graph forming section 123 may compute second moving averages of the average intensities for second subsets of the rows by dividing the intensities by a thickness of a vascular wall. As shown in FIG. 7, the third graph forming section 123 may form a third graph of the first moving averages with respect to the row of pixels in the ultrasound image. The second moving averages $MA_{21}$-$MA_{2m}$ may be computed by using the following equation (3).

$$MA_{21} = \frac{f_1 + f_2 + \ldots + f_{j-1} + f_j}{j} \quad (3)$$

$$MA_{22} = \frac{f_2 + f_3 + \ldots + f_j + f_{j+1}}{j}$$

$$\vdots$$

$$MA_{2m} = \frac{f_{m-j+1} + f_{m-j+2} + \ldots + f_{m-1} + f_m}{j}$$

wherein "j" indicates the number of pixels included within the thickness of the vascular wall and "m" indicates the number of second moving averages. Generally, the thickness of the carotid wall ranges from 0.5 to 1.5 mm. For example, assuming that the thickness of the carotid wall is 1 mm and the height of the pixel is 0.5 mm, "j" becomes 2. FIG. 7 shows the third graph of the second moving averages with respect to the row of pixels in the ultrasound image. In FIG. 7, "$I_m$," represents an inflection point having the largest second moving average on the third graph.

The IMT measuring region setting section 124 may detect the inflection points $I_1$ and $I_m$, on the second and third graphs. The IMT measuring region setting section 124 may detect a plurality of inflection points at which an inclination of curvatures on the second graph changes and selects the inflection point $I_1$ having the smallest first moving average value. The IMT measuring region setting section 124 may detect a plurality of inflection points at which an inclination of curvatures on the third graph changes and selects the inflection point $I_m$ having the largest second moving average value. The IMT measuring region setting section 124 may set the inflection points $I_1$ and $I_m$ on the ultrasound image. In one embodiment, the IMT measuring region setting section 124 may set the region between $I_1$ and $I_m$. as the IMT measuring region.

Referring back to FIG. 1, the display unit 130 may display the ultrasound image on which the IMT measuring region is set. The display unit 130 may include liquid crystal display (LCD), cathode ray tube (CRT) and the like Any reference in this specification to "one embodiment," "an embodiment," "example embodiment," "illustrative embodiment," etc. means that a particular feature, structure or characteristic described in connection with the embodiment is included in at least one embodiment of the present invention. The appearances of such phrases in various places in the specification are not necessarily all referring to the same embodiment. Further, when a particular feature, structure or characteristic is described in connection with any embodiment, it is submitted that it is within the purview of one skilled in the art to affect such feature, structure or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An ultrasound system, comprising:
   an ultrasound probe configured to transmit ultrasound signals to a target object and receive ultrasound echo signals reflected from the target object; and
   a processor configured to:
   (i) form an ultrasound image including a plurality of pixels based on the ultrasound echo signals received by the ultrasound probe, each of the plurality of pixels having an intensity of gray level, the plurality of pixels being arranged in a plurality of rows,
   (ii) compute a specific value of intensities of the pixels at each one of the rows in the ultrasound image, and form a first graph using the computed specific value of intensities of the pixels at each one of the rows, (iii) compute a first number of pixels included within a predetermined thickness of a blood vessel and determine first subsets by sequentially shifting the specific value one by one from a first one of the rows, each first subset having the first number of specific values, (iv) compute first moving averages of the specific values included in the respective first subsets, and form a second graph showing the computed first moving averages, (v) compute a second number of pixels included within a predetermined thickness of a vascular wall and determine second subsets by sequentially shifting the specific value one by one from the first row, each second subset having the second number of specific values, and (vi) compute second moving averages of the specific values included in the respective second subsets, and form a third graph showing the computed second moving averages, (vii) set an intima-media thickness (IMT) measuring region by using inflection points from the second and third graphs; and (viii) display the ultra sound image and the set IMT measuring region.

2. The ultrasound system of claim 1, wherein the specific value of intensities is obtained by averaging the intensities of the pixels per each row in the ultrasound image.

3. The ultrasound system of claim 1, wherein the specific value of intensities is obtained by summing the intensities of the pixels per each row.

4. The ultrasound system of claim 1, wherein the processor is further configured to detect a plurality of inflection points at which an inclination of curvatures on the second graph changes, select a first inflection point having a smallest first moving average among the inflection points in the second graph, detect a plurality of inflection points at which an inclination of curvatures on the third graph changes, select a second inflection point having a largest second moving average among the inflection points in the third graph, and set the IMT measuring region based on the first and second inflection points on the ultrasound image.

5. The ultrasound system of claim 1, wherein the first number is determined by dividing the predetermined thickness of the blood vessel by a size of the pixel.

6. The ultrasound system of claim 1, wherein the second number is determined by dividing the predetermined thickness of the vascular wall by a size of the pixel.

7. A method of setting an intima-media thickness (IMT) measuring region in an ultrasound system, comprising:
   a) obtaining an ultrasound image including a plurality of pixels by an ultrasound diagnosis unit comprising an ultrasound probe within the ultrasound system, the plurality of pixels being arranged in a plurality of rows;
   b) computing a specific value of intensities of the pixels at each one of the rows in the ultrasound image and forming a first graph using the computed specific value of intensities of the pixels at each one of the rows, by a processor within the ultrasound system;
   c) computing a first number of pixels included within a predetermined thickness of a blood vessel and determining first subsets by sequentially shifting the specific value one by one from a first one of the rows, each first subset having the first number of specific values by the processor within the ultrasound system;
   d) computing first moving averages of the specific values included in the respective first subsets, and forming a second graph showing the computed first moving averages by the processor within the ultrasound system;
   e) computing a second number of pixels included within a predetermined thickness of a vascular wall and determining second subsets by sequentially shifting the specific value one by one from the first row, each second subset having the second number of specific values by the processor within the ultrasound system;
   f) computing second moving averages of the specific values included in the respective second subsets, and forming a third graph showing the computed second moving averages by the processor within the ultrasound system;
   g) detecting inflection points from the second and third graphs by the processor within the ultrasound system;
   h) setting an intima-media thickness (IMT) measuring region by using the inflection points by the processor within the ultrasound system; and
   i) displaying the ultrasound image and the set IMT measuring region.

8. The method of claim 7, wherein the step b) comprises averaging the intensities of the pixels per each row in the ultrasound image to obtain the specific value by the processor.

9. The method of claim 7, wherein the step b) comprises summing the intensities of the pixels per each row to obtain the specific value by the processor.

10. The method of claim 7, wherein the detecting step g) comprises:
   g1) detecting a plurality of inflection points at which an inclination of curvatures on the second graph changes;
   g2) selecting a first inflection point having a smallest first moving average among the plurality of inflection points in the second graph;
   g3) detecting a plurality of inflection points at which an inclination of curvatures on the third graph changes; and
   g4) selecting a second inflection point having a largest second moving average among the plurality of inflection points in the third graph.

11. The method of claim 10, wherein the setting step h) further comprises setting the IMT measuring region based on the first and second inflection points on the ultrasound image.

12. The method of claim 7, wherein the first number is determined by dividing the predetermined thickness of the blood vessel by a size of the pixel.

13. The method of claim 7, wherein the second number is determined by dividing the predetermined thickness of the vascular wall by a size of the pixel.

14. A non-transitory computer readable medium comprising instructions that, when executed by a processor, performs a method of setting intima-media thickness (IMT) measuring region by causing the processor to perform steps comprising:
   a) obtaining an ultrasound image, which includes a plurality of pixels arranged in a plurality of rows;
   b) computing a specific value of intensities of the pixels at each one of the rows in the ultrasound image, and forming a first graph using the computed specific value of intensities of the pixels at each one of the rows;
   c) computing a first number of pixels included within a predetermined thickness of a blood vessel and determining first subsets by sequentially shifting the specific value one by one from a first one of the rows, each first subset having the first number of specific values;

d) computing first moving averages of the specific values included in the respective first subsets, and forming a second graph showing the computed first moving averages;

e) computing a second number of pixels included within a predetermined thickness of a vascular wall and determining second subsets by sequentially shifting the specific value one by one from the first row, each second subset having the second number of specific values;

f) computing second moving averages of the specific values included in the respective second subsets, and forming a third graph showing the computed second moving averages;

g) detecting inflection points from the second graph and the third graph;

h) setting an intima-media thickness (IMT) measuring region by using the inflection points; and i) displaying the ultrasound image and the set IMT measuring region.

15. The non-transitory computer readable medium of claim 14, wherein the detecting step g) comprises:

g1) detecting a plurality of inflection points at which an inclination of curvatures on the second graph changes;

g2) selecting a first inflection point having a smallest first moving average among the plurality of inflection points in the second graph;

g3) detecting a plurality of inflection points at which an inclination of curvatures on the third graph changes; and g4) selecting a second inflection point having a largest second moving average among the plurality of inflection points in the third graph.

* * * * *